(12) United States Patent
Desrosiers et al.

(10) Patent No.: US 10,920,263 B2
(45) Date of Patent: Feb. 16, 2021

(54) METHODS, COMPOSITIONS AND KITS FOR DETERMINING CLEANNESS OF A SURFACE

(71) Applicant: Sani-Marc Inc., Victoriaville (CA)

(72) Inventors: Dominic Desrosiers, Sainte-Eulalie (CA); Patrick Marchand, Victoriaville (CA)

(73) Assignee: Sani-Marc Inc., Victoriaville (CA)

( * ) Notice: Subject to any disclaimer, the term of this patent is extended or adjusted under 35 U.S.C. 154(b) by 993 days.

(21) Appl. No.: 15/296,299

(22) Filed: Oct. 18, 2016

(65) Prior Publication Data

US 2018/0105861 A1    Apr. 19, 2018

Related U.S. Application Data

(60) Provisional application No. 62/301,716, filed on Mar. 1, 2016.

(51) Int. Cl.

| C12Q 1/30 | (2006.01) |
| C12N 9/08 | (2006.01) |
| C01B 15/01 | (2006.01) |
| C12Q 1/04 | (2006.01) |
| C11D 1/75 | (2006.01) |

(52) U.S. Cl.
CPC .............. C12Q 1/30 (2013.01); C01B 15/01 (2013.01); C12N 9/0065 (2013.01); C12Q 1/04 (2013.01); C12Y 111/01006 (2013.01); C11D 1/75 (2013.01)

(58) Field of Classification Search
None
See application file for complete search history.

(56) References Cited

U.S. PATENT DOCUMENTS

| 5,431,843 A * | 7/1995 | Mitchell ................ C11D 3/391 134/30 |
| 6,479,454 B1 | 11/2002 | Smith et al. |
| 6,699,828 B1 | 3/2004 | de Buzzaccarini et al. |
| 7,569,359 B2 | 8/2009 | McDonnell et al. |
| 7,674,602 B2 | 3/2010 | Kadurugamuwa et al. |
| 2005/0042757 A1 | 2/2005 | Famme |
| 2007/0231200 A1* | 10/2007 | Lin ........................ A61L 2/16 422/30 |
| 2009/0208996 A1 | 8/2009 | Kadurugamuwa |
| 2014/0274853 A1* | 9/2014 | Ortmann ............ C11D 3/38663 510/195 |

FOREIGN PATENT DOCUMENTS

| CN | 101324630 A | 12/2008 |
| EP | 0105747 A1 | 4/1984 |
| EP | 0184260 A1 | 11/1986 |
| EP | 2902497 A1 | 5/2015 |
| FR | 2611744 A1 | 2/1987 |
| JP | 61162199 A1 | 7/1986 |
| JP | 2010059296 A * | 3/2010 |
| WO | 2001034831 A2 | 5/2001 |
| WO | 2014049282 A1 | 3/2014 |

OTHER PUBLICATIONS

Brown et al., Proc. Natl. Acad. Sci., 1989, 86:2516-2520. (Year: 1989).*
Wikipedia-Sodium dodecyl sulfate printout, downloaded on Nov. 20, 2019 from the website https://en.wikipedia.org/wiki/Sodium_dodecyl_sulfate (Year: 2019).*
Mollers et al., Carbohydrate Research, 2017, 448: 182-186. (Year: 2017).*
Sha et al., J. Chem. Technol. Biotechnol. 2012, 87: 368-373 (Year: 2012).*
Product data sheet—Terminox Ultra catalase from Novozymes, 2014 (Year: 2014).*
Wikipedia—Lauryldimethylamine oxide printout downloaded on Oct. 22, 2019 from https://en.wikipedia.org/wiki/Lauryldimethylamine_oxide (Year: 2019).*
Bartoszek et al., The Study of pH Influence on Bovine Liver Catalase by Means of UV-VIS Spectroscopy and Spin Labelling Method, Polish J. of Environ Stud., Sep. 20-23, 2006, vol. 15 No. 4A, pp. 41-43.
European Patent Office Examiners Communiction pursuant to Article 94(3) EPC for EP Application No. 16194450.9-1118, dated Aug. 8, 2018.
Martowitono, "Cleaning and Disinfection on Fish Contact Surfaces Table of Contents," United Nations University Fisheries Training Programs, Final Project Jan. 1, 2011, Publication, pp. 1-25, http://www.unuftp.is/static/fellows/document/netty2011prf.pdf.
AAT Bioquest®, Amplite™ Fluroimetric Catalase Assay Kit, *Red Fluorescence*, Product Technical Information Sheet, Jun. 1, 2012, 3 pages, http://www.interchim.fr/ft/G/GCX680.pd.
European Search Report for application No. EP 16 19 4450, dated Mar. 16, 2017.

* cited by examiner

*Primary Examiner* — Allison M Fox
*Assistant Examiner* — Qing Xu
(74) *Attorney, Agent, or Firm* — Heslin Rothenberg Farley & Mesiti P.C.

(57) ABSTRACT

The invention relates to methods, compositions and kits for determining the cleanness of a surface. Described herein is a kit for determining the cleanness of a surface comprising an enzymatic solution comprising catalase; and a developer solution comprising hydrogen peroxide. Described also is a method for determining the cleanness of a surface comprising: applying on a zone of a surface to be cleaned an enzymatic solution comprising catalase and letting it dry; after cleaning said surface, applying on said zone a developer solution comprising hydrogen peroxide; and detecting a catalytic reaction between remaining catalase and hydrogen peroxide, wherein presence of a catalytic reaction is indicative of a surface not properly cleaned. Also provided are specific enzymatic solutions and developer solutions for the kits and methods.

14 Claims, 5 Drawing Sheets

METHODS, COMPOSITIONS AND KITS FOR DETERMINING CLEANNESS OF A SURFACE

RELATED APPLICATION

Figure 1:
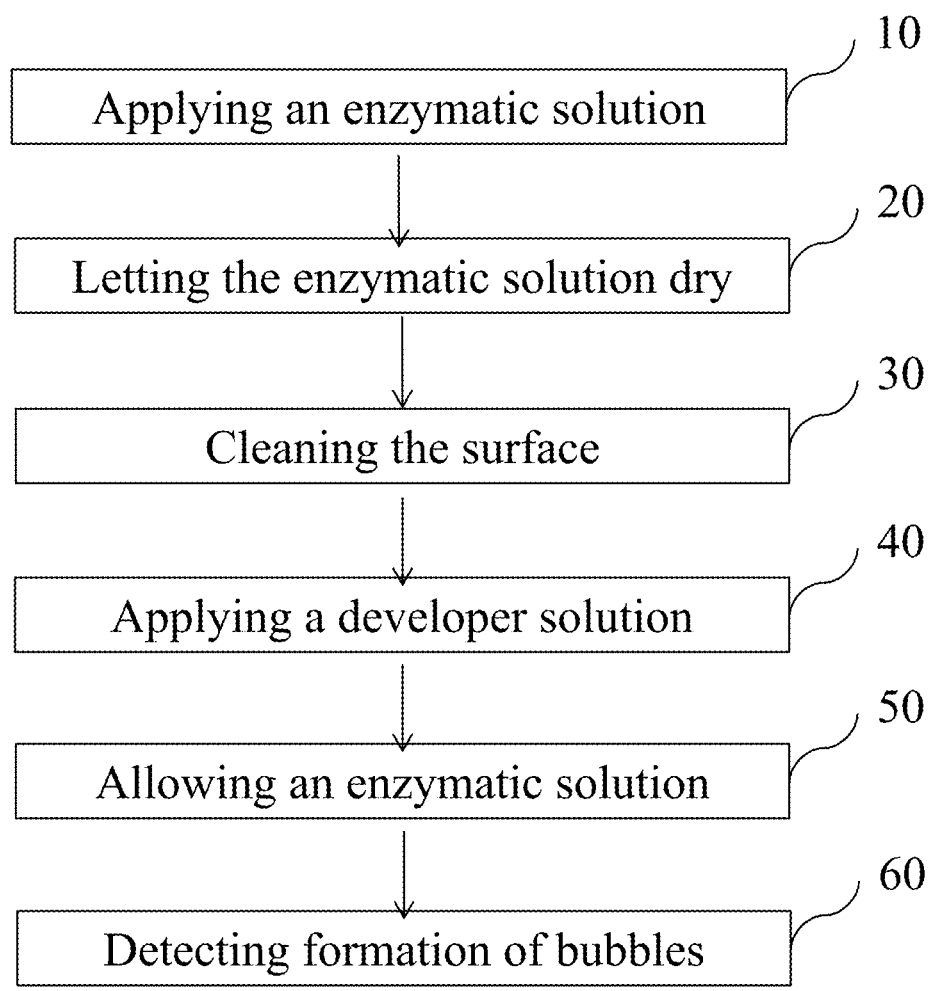

This application claims priority to U.S. provisional application No. 62/301,716 filed on Mar. 1, 2016, the contents of which is incorporated herein by reference in its entirety.

FIELD OF THE INVENTION

The invention relates to the field of hygiene and more particularly to surface cleaning.

BACKGROUND OF THE INVENTION

In many highly contaminated environments such as hospitals, restaurants, food processing facilities, slaughterhouses, etc., it is extremely important to make sure that cleaning has been done properly. For instance, nosocomial infections are a major problem in hospitals in Canada and around the world. Every year, in Canada alone, more than 200000 patients will get a nosocomial infection and nearly ten thousand of these patients will die as a result. Surface cleanness is also critical in other environments such as laboratories where the contaminants may include not only bacteria and viruses, but also chemicals and radioactive compounds.

One of the reasons for the inadequate cleaning is the lack of suitable tools that would ensure better control of the quality of cleaning. Indeed, microorganisms and radioactivity are not visible to the naked eye and it is extremely difficult to assess cleanness. Because it is difficult to ensure that the cleaning has been done properly, some areas to be cleaned may be neglected, intentionally or not.

Some tools already exist to try to ensure adequate cleaning of a surface. For instance, there are different methods in which one will make some "spot check" in order to detect the presence of remaining bacteria or viruses on surfaces that have been previously cleaned. These may include taking smears for later analysis in a laboratory or marking the surface with a pen having an ink detectable under UV light. However, these methods have numerous deficiencies including the high number of smears that have to be taken to cover a large surface, the delays and cost associated with the samples than have to be analyzed in a remote place or with special equipment, the risks of cross-contaminations, etc.

The present invention concerns methods, compositions and kits for determining the cleanness of a surface that are based on the reaction of decomposition of hydrogen peroxide by catalase:

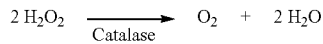

The above chemical reaction is well known and it has been applied by others for the detection of microorganism and biofilms, for instance U.S. Pat. No. 7,764,602; International PCT publication WO 2014/019182; European patent publications EP 0 105 747 and EP 2 902 497, and French patent publication FR 2 611 744. However, the approaches described in these patent documents have different limitations, notably the fact that they rely on the presence of catalase in the bacteria. Accordingly, these are all dependent on the presence of catalase-positive bacteria and they are of no utility for detecting microorganisms that have undetectable level of catalase or that produce no catalase at all, let alone the detection of contaminated radioactive surfaces.

There is thus a need for improved approaches and techniques for determining the cleanness of a surface, and more particularly surfaces from contaminated environments like those found in hospitals, restaurants, food processing facilities, slaughterhouses, laboratories, etc.

There is also a need for reliable, effective and cheap approaches for improving surface hygiene and assessing cleanness of a surface that may have been contaminated by different types of microorganisms (e.g. bacteria, viruses, yeast, etc.) or by any other type of contaminants (e.g. radioactivity, chemicals, proteins, fat, blood, urine, excrement, biological matters, mineral deposits, etc.).

The present invention addresses these needs, as it relates to methods, compositions and kits for determining cleanness of a surface.

Features of the invention will be apparent from review of the disclosure, drawings and description of the invention below.

BRIEF SUMMARY OF THE INVENTION

The invention relates to methods, compositions and kits for determining the cleanness of a surface.

According to one aspect, the invention relates to the use of an enzymatic solution comprising catalase for determining the cleanness of a surface. Preferably, this is achieved in conjunction with a developer solution allowing visual detection of the catalase.

According to another aspect, the invention relates to a kit for determining the cleanness of a surface, the kit comprising an enzymatic solution comprising catalase and a developer solution comprising hydrogen peroxide.

According to another aspect, the invention relates to a method for determining the cleanness of a surface comprising:
  applying on a zone of a surface to be cleaned an enzymatic solution comprising catalase and letting it dry;
  after cleaning said surface, applying on said zone a developer solution comprising hydrogen peroxide; and
  detecting a catalytic reaction between remaining catalase and hydrogen peroxide, wherein presence of a catalytic reaction is indicative of a surface not properly cleaned.

The enzymatic solution may comprises about 40 U/g to about 900000 U/g catalase, about 400 U/g to about 750000 U/g catalase, or about 1000 U/g to about 500000 U/g catalase, or about 4000 U/g to about 20000 U/g catalase.

The enzymatic solution may also comprise one or more solvents. The enzymatic solution may also comprise one or more components including, but not limited to surfactants (ionic or non-ionic), buffers, preservatives, stabilizers and thickening agents.

The developer solution may comprise about 0.05% w/w to about 50% w/w hydrogen peroxide, or about 0.5% w/w to about 10% w/w hydrogen peroxide, or about 1% w/w to about 5% w/w hydrogen peroxide.

The developer solution may also comprise one or more components including, but not limited to, foaming agents, dyes, buffers, preservatives, stabilizers and thickening agents.

The invention also relates to particular enzymatic and developer solutions like the ones defined hereafter in Table 1A, Table 1B, Table 2A, Table 2B, Table 3, and Table 4.

The kits, methods and uses according to the invention may assist in assessing proper removal of microorganisms (e.g. bacteria, viruses, yeast, etc.), chemicals, or radioactive compounds, biological materials (e.g. food, proteins, fat, blood, urine, excrements, and other biological matters), minerals(e.g. mineral deposits) and the like from an allegedly cleaned surface. The surface may be found for instance in hospitals, restaurants, food processing facilities, slaughterhouses and laboratories.

As it will be appreciated, the present invention possess numerous advantages, including, but not limited to: ease of use; cost effectiveness; allowing a "real-time" visual detection; does not damage the surfaces; easy cleaning; prevent cross-contamination; provides aqueous solutions that are stable at a broad range of temperature (e.g. about −15° C. to about 40° C.) and provides for a fast evaporation of the enzymatic solution.

BRIEF DESCRIPTION OF THE DRAWINGS (OR FIGURES)

In order for the invention to be readily understood, embodiments of the invention are illustrated by way of example in the accompanying drawings.

FIG. 1 is a flow chart illustrating the steps of a method for determining cleanness of a surface, according to one embodiment of the present invention.

FIG. 2A, FIG. 2B, FIG. 2C, and FIG. 2D is a panel showing pictures of a particular zone of a surface which has been sprayed by an enzymatic solution and by a developer solution, according to one embodiment the invention. The sprayed zone is delimited by a rectangle defined with a tape. (A)=surface freshly sprayed with the enzymatic solution; (B)=surface on which the enzymatic solution has dried; (C)=uncleaned surface freshly sprayed with the developer solution; (D)=cleaned surface freshly sprayed with the developer solution.

Figure 3:
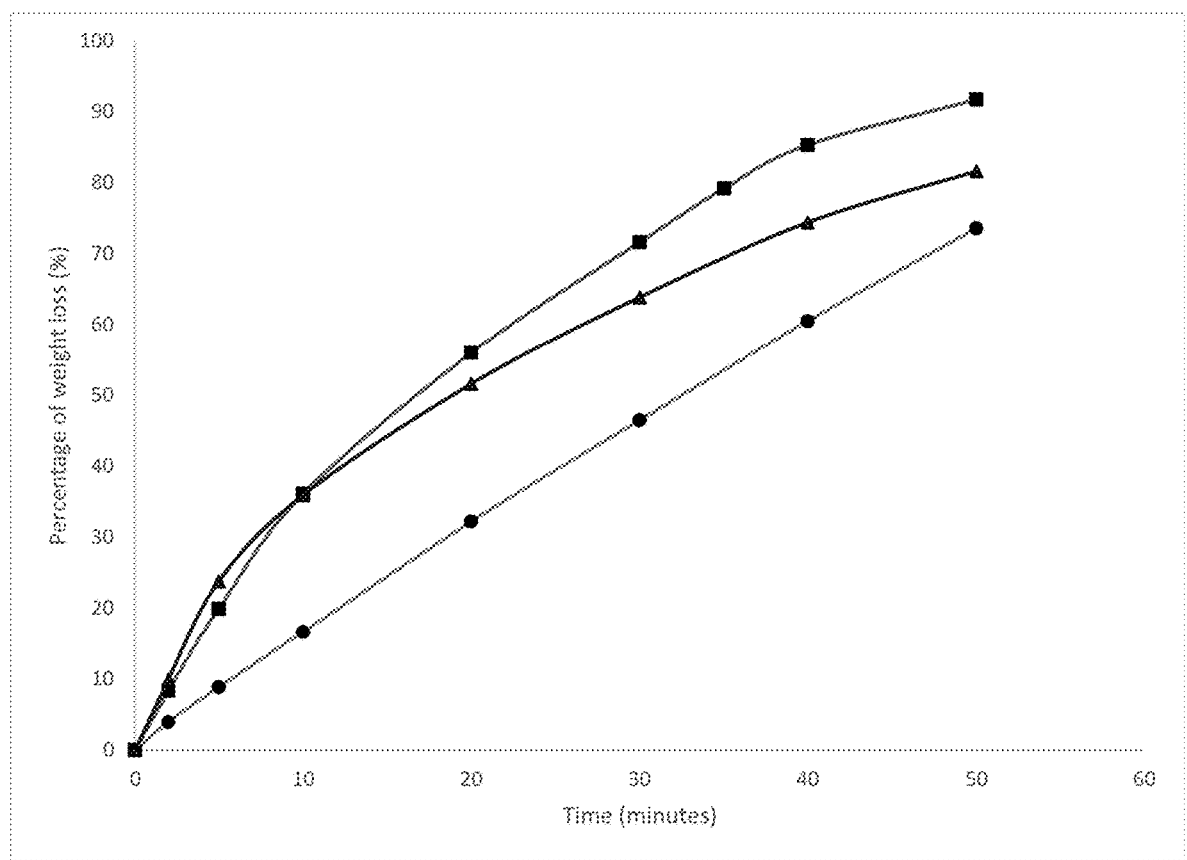

FIG. 3 is a line graph showing time of evaporation of the enzymatic solution, according to the formulations of Table 2: Formulation 2294.27 (■); Formulation 3294.27 (●); Formulation 1296.27 (▲).

Figure 4:
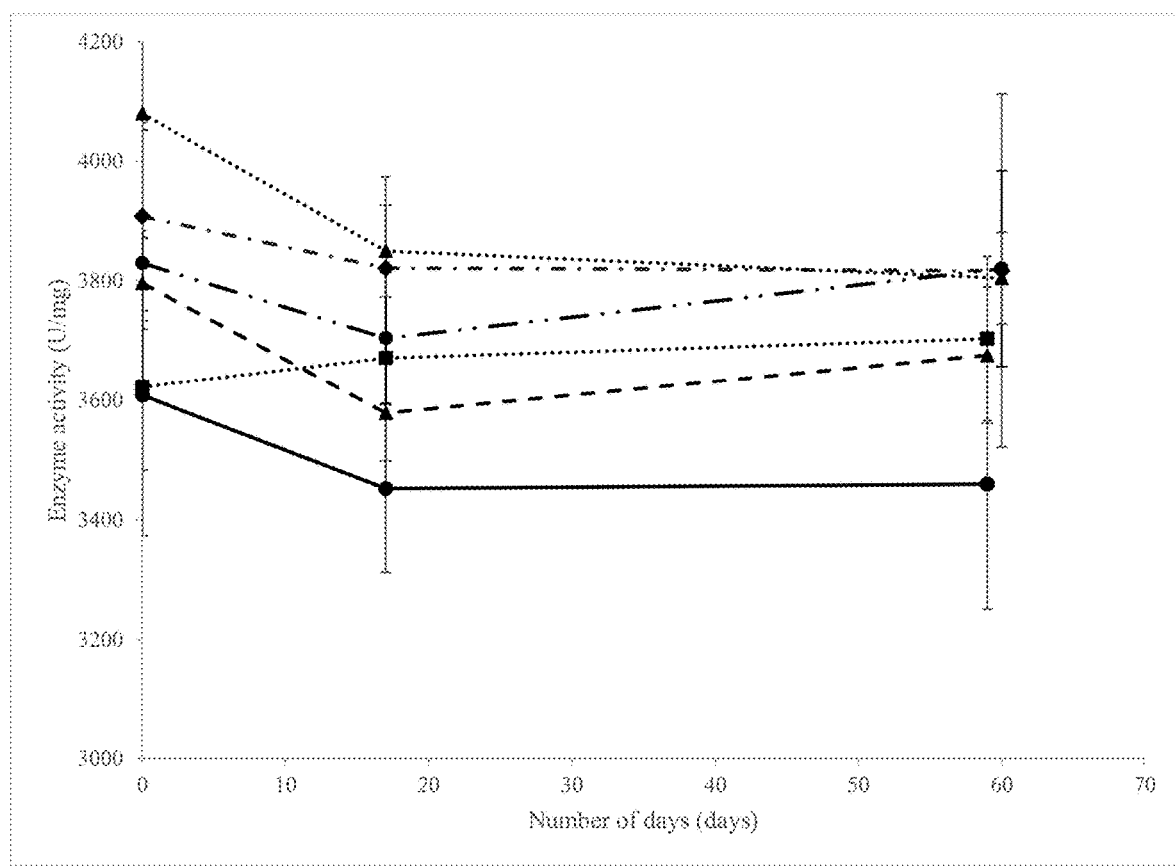

FIG. 4 is a line graph showing catalase activity over time, in the enzymatic solution according to the formulations of Table 3, comprising Propylene glycol at 0% (-●-), 0.5% (-▲-), 1% (-■-), 1.5% (-◆-), 2% (-●-) and 2.5% (-▲-).

Further details of the invention and its advantages will be apparent from the detailed description included below.

DETAILED DESCRIPTION OF PREFERRED EMBODIMENTS

In the following description of the embodiments, references to the accompanying drawings are by way of illustration of an example by which the invention may be practiced. It will be understood that other embodiments may be made without departing from the scope of the invention disclosed.

The invention pertains to methods, compositions and kits for determining the cleanness of a surface that are based on the decomposition of hydrogen peroxide by catalase.

Briefly, according to the principles of the present invention cleanness of a surface is assessed by "soiling" a zone of the surface to be cleaned with catalase and, after cleaning of the surface has been done, detecting presence of residual catalase on the allegedly cleaned surface.

Figure 2A:
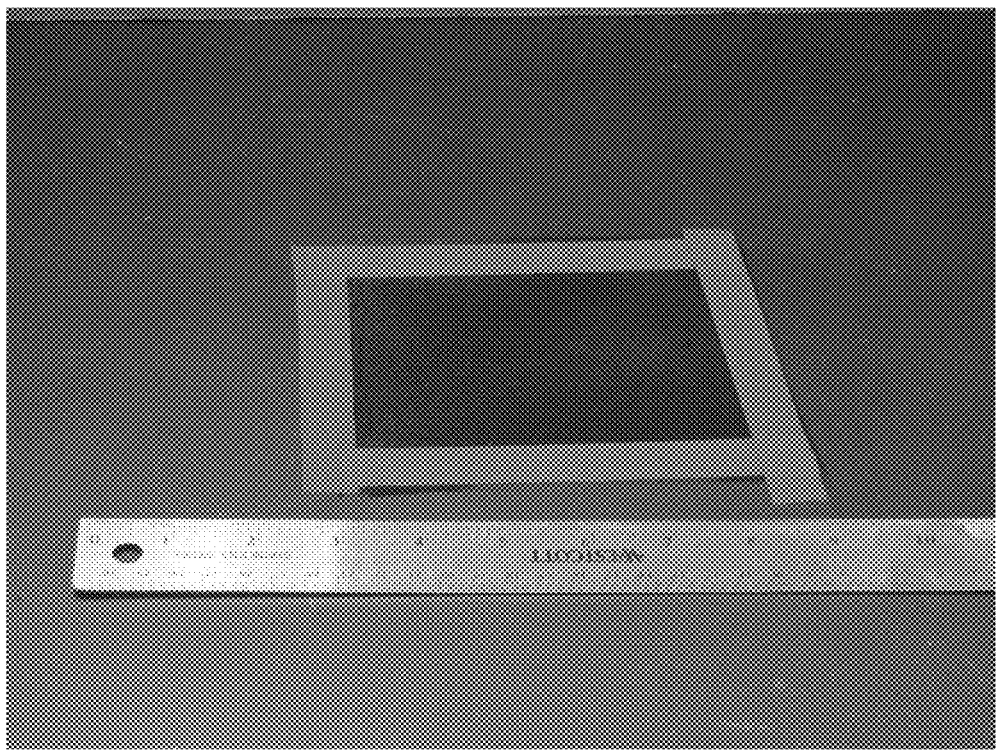
Figure 2B:
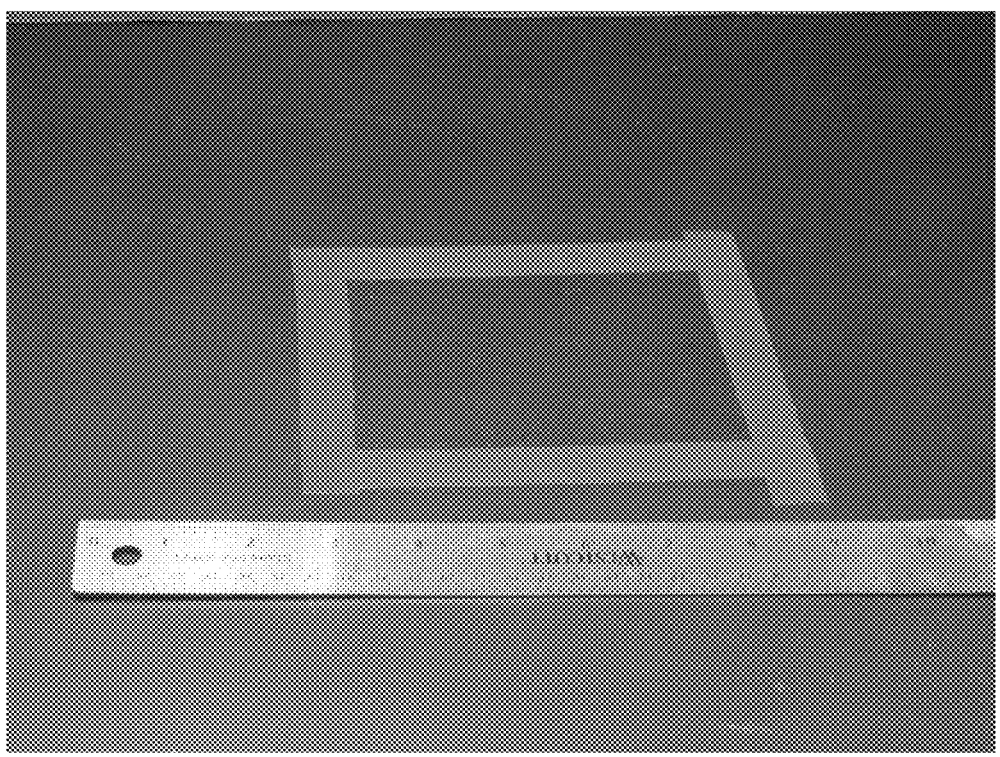
Figure 2C:
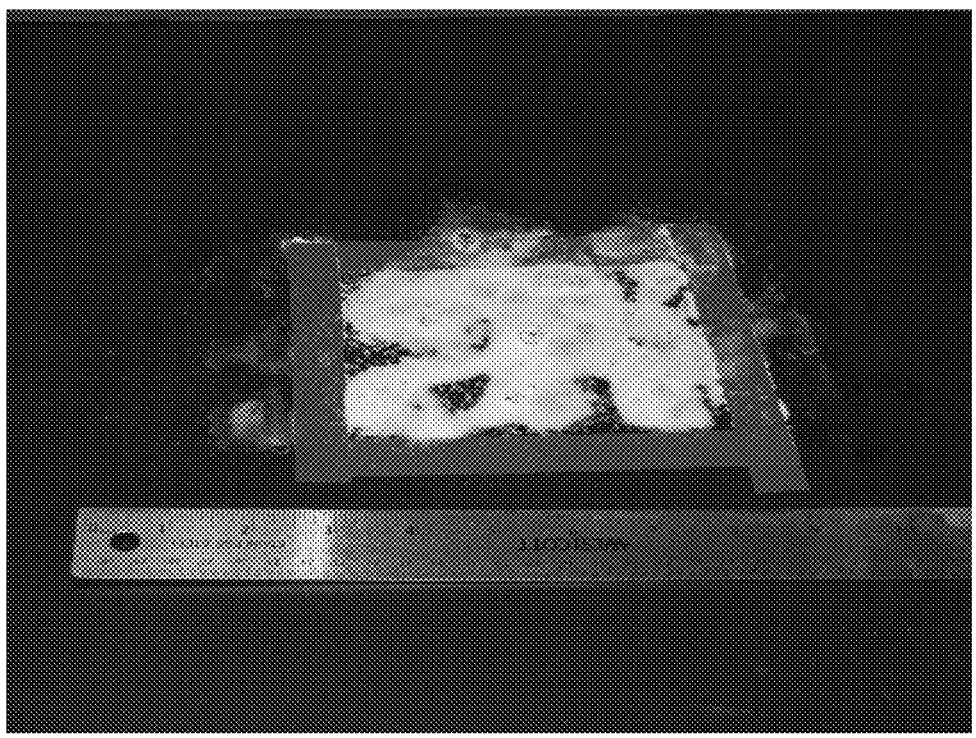
Figure 2D:
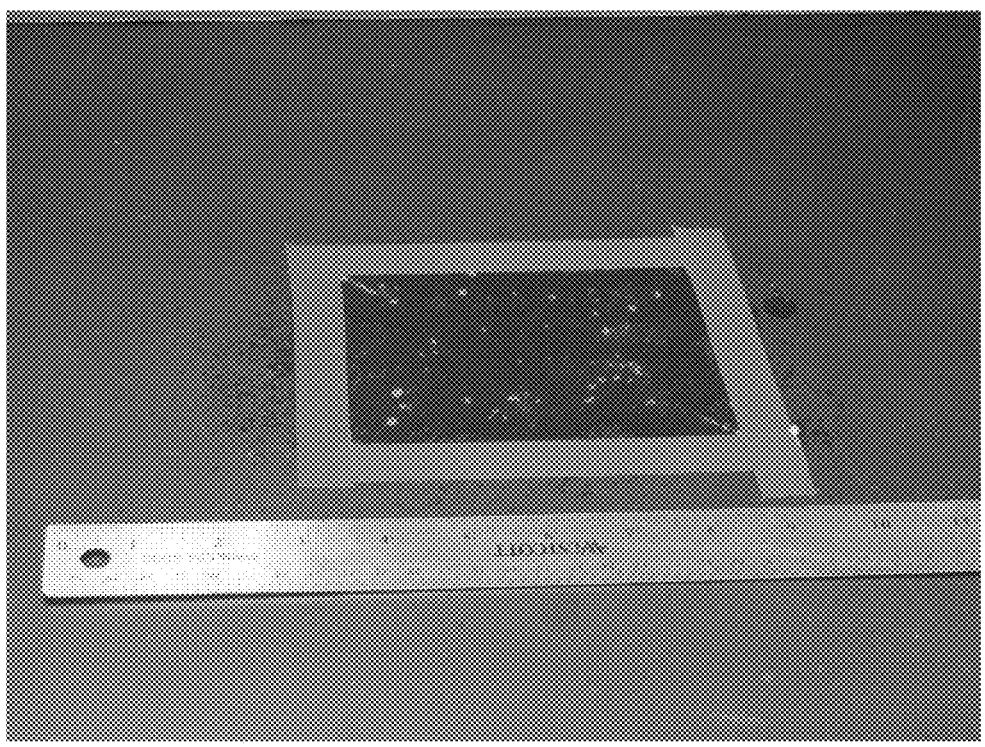

Referring to FIG. 1 and FIG. 2, prior to cleaning by a housekeeping person or concierge, a first person (e.g. supervisor or controller) applies an enzymatic solution comprising catalase on a given zone of the surface to be cleaned (10) (see also FIG. 2A). The applied enzymatic solution is let dried (20) so that it becomes practically invisible, as shown in FIG. 2B. The housekeeping person or concierge is let to do his job (30) and, after cleaning has been performed, the first person applies a developer solution (40) comprising hydrogen peroxide on the same zone of the allegedly cleaned surface. If the surface has not been cleaned properly, the hydrogen peroxide will react with remaining catalase (50), causing the formation of "bubbles" or a foam that will be easily visible to the naked eye (60) as shown in FIG. 2C. To the contrary, if the surface is perfectly clean there will be no catalase left and no bubble will form as shown in FIG. 2D.

Enzymatic Solution

One essential component of the enzymatic solution is a source of catalase. As is known, catalase is a common enzyme found in nearly all living organisms exposed to oxygen (such as bacteria, plants, and animals). It catalyzes the decomposition of hydrogen peroxide to water and oxygen as illustrated hereinbefore. According to the invention, the catalase may be obtained from different sources including, but not limited to, fungi (e.g. *Aspergillus niger, Aspergillus oryzae*), liver (e.g. bovine), plants and bacteria. The catalase may be obtained from commercial sources such as Sigma Aldrich, Novozymes (e.g. Catazyme™ 25L, Terminox™ Ultra 50L, Terminox™ Ultra 200L) and other suppliers like VWR, Fisher scientific, Dupont, etc.

The enzymatic activity of the catalase may be measured in enzyme unit (U). As used herein, one U is defined as the amount of catalase enzyme that catalyzes the conversion of 1 micro mole of hydrogen peroxide per minute in water, at pH 7, at 25° C., at a concentration of 26 mM hydrogen peroxide.

In embodiments, the enzymatic solution comprises about 40 U/g to about 900000 U/g catalase, about 400 U/g to about 750000 U/g catalase, or about 1000 U/g to about 500000 U/g catalase, or about 4000 U/g to about 20000 U/g catalase.

The enzymatic solution may also comprise one or more solvents to accelerate evaporation. Examples of envisioned solvents include, but are not limited to, methanol (MeOH), ethanol (EtOH) and isopropanol (isopropyl alcohol or IPA). In embodiments, the enzymatic solution comprises about 5% w/w to about 65% w/w solvent or about 25% w/w to about 50% w/w solvent.

The enzymatic solution may also comprise a surfactant (ionic or non-ionic) to accelerate evaporation. As is known, surfactants improve evaporation by reducing the tension of surface causing the product to extend more easily over the surface. Examples of envisioned ionic surfactants include, but are not limited to, sodium dodecyl sulfate (Stepanol™ WA Extra), sodium dodecylbenzene sulfonate (Bio-Soft™ S-101), sodium linear olefin sulfonate (Bio-Terge™ AS-40K), sodium caprylyl sulfonate (Bio-Terge™ PAS-8S), sodium laureth sulfate (Steol™ CS-230). Examples of envisioned non-ionic surfactants include, but are not limited to, linear ethoxylated alcohols (e.g. Bio-Soft™ N1-7, Bio-Soft™ 91-6, Bio-Soft™ E678). In embodiments, the enzymatic solution comprises between 0.01% w/w to 5% w/w surfactant, or between 0.01% w/w to 2.5% w/w surfactant, or between 0.05% w/v to 0.5% w/w surfactant.

The pH of the enzymatic solution may vary between 4 and 11. The pH may be selected in accordance with the pH optimum for the particular catalase in the solution and, preferably, also for avoiding damaging the surfaces. In embodiments, the pH is preferably between 4.5 and 7.5 or more preferably between 5.7 and 6.3, or even more preferably about 6.0.

To maintain a proper pH, the enzymatic solution may comprise a buffer. Examples of envisioned buffers include, but are not limited to, citrate buffer, phosphate buffer and phosphate citrate buffer. In embodiments, the enzymatic solution comprises about 0.05% w/w to about 5% w/w buffer, or about 0.1% w/w to about 2% w/w buffer, or about 0.5% w/w to about 1.5% w/w buffer.

The enzymatic solution may also comprise one or more preservatives. Examples of envisioned preservatives include, but are not limited to, chloro-2-methyl-4-isothiazolin-3-one (e.g. Kathon™ CG/ICP). In embodiments, the enzymatic solution comprises about 0.01 ppm to about 100 ppm stabilizer, or about 0.05 ppm to about 50 ppm stabilizer, or about 0.1 ppm to about 10 ppm stabilizer.

The enzymatic solution may also comprise one or more stabilizers, including stabilizer(s) of catalase activity. Examples of envisioned stabilizers include, but are not limited to, propylene glycol, boric acid. In embodiments, the enzymatic solution comprises about 0.01% w/w to about 10% w/w stabilizer, or about 0.1% w/w to about 5% w/w stabilizer, or about 0.5% w/w to about 2% w/w stabilizer.

The enzymatic solution may comprise one or more thickening agents in order to improve adhesion of the enzymatic solution on vertical surfaces. Examples of envisioned thickening agents include, but are not limited to, Xanthan gum (e.g. Kelzan™ T), cross-linked polyacrylic acid polymer (e.g. Ultrez™ 10). In embodiments, the enzymatic solution comprises about 0.05% w/w to about 2% w/w thickening agent, or about 0.05% w/w to about 1% w/w thickening agent, or about 0.1% w/w to about 0.5% w/w thickening agent.

According to one particular embodiment, the enzymatic solution according to the invention is composed according to the following table:

TABLE 1A

| Enzymatic solution | | | |
| --- | --- | --- | --- |
| Components | CAS number | Role | Concentration (% w/w) |
| Catalase | 9001-05-2 | enzyme | 0.001-19 (about 42 U/g to about 806 000 U/g) |
| Propylene glycol | 57-55-6 | solvent/stabilizer | 0-10 |
| Chloro-2-methyl-4-isothiazolin-3-one | 26172-55-4 | preservative | 0-0.01 |
| Ethoxylated C12-15 alcohols | 68131-39-5 | surfactant | 0-5 |
| Isopropanol | 67-63-0 | solvent | 0-99.999 (To complete to 100% with water, if any) |
| Demineralized water | — | solvent | 0-99.999 (To complete to 100% with isopropanol, in any) |

According to a preferred embodiment, the enzymatic solution according to the invention is composed according to the following table:

TABLE 1B

| Enzymatic solution | | | |
| --- | --- | --- | --- |
| Components | CAS number | Role | Concentration (% w/w) |
| Catalase | 9001-05-2 | enzyme | 0.11 (4780 U/g) |
| Propylene glycol | 57-55-6 | solvent/stabilizer | 1 |
| Chloro-2-methyl-4-isothiazolin-3-one | 26172-55-4 | preservative | 0.0004 |
| Ethoxylated C12-15 alcohols | 68131-39-5 | surfactant | 0.085 |
| Isopropanol | 67-63-0 | solvent | 30 |
| Demineralized water | — | solvent | 68.9146 |
| pH | | Adjusted to about 6 | |

The enzymatic solution may be formulated as an aqueous solution or as a powder for later dissolution in a suitable aqueous solution (e.g. water). The enzymatic solution may be formulated as a ready to use solution or as a liquid concentrate (e.g. 2×, 3×, 4×, 5×, 10× etc.) for further dilution. For a composition formulated as a liquid and/or solid ingredient may be mixed with a predetermined volume of filtered or distilled water. If necessary, the resulting mixed solution may be adjusted to the desired pH by addition of suitable acidifying agents.

Developer Solution

A related aspect of invention relates to a developer solution. As indicated hereinbefore, the role of the developer solution is to provide a source of hydrogen peroxide to react with catalase provided by the enzymatic solution.

Accordingly, one essential component of the developer solution is a source of hydrogen peroxide. In embodiments, the developer solution comprises about 0.05% w/w to about 50% w/w hydrogen peroxide, or about 0.5% w/w to about 10% w/w hydrogen peroxide, or about 1% w/w to about 5% w/w hydrogen peroxide.

The developer solution may also comprise one or more thickening agents in order to improve adhesion of the developer solution on vertical surfaces. Examples of envisioned thickening agents include, but are not limited to, Xanthan gum (e.g. Kelzan™ T), cross-linked polyacrylic acid polymer (e.g. Ultrez™ 10). In embodiments, the developer solution comprises between 0.05% w/w to 2% w/w thickening agent, or between 0.1% w/w to 1% w/w thickening agent, or between 0.2% w/w to 0.8% w/w thickening agent.

The pH of the developer solution may vary between 4 and 11. The pH may be selected in accordance with the pH optimum for the hydrogen peroxide stability and, preferably, also for avoiding damaging the surfaces. In embodiments, the pH is preferably between 4 and 9 and more preferably between 6 and 8, or even more preferably about 7.5.

The developer solution may also comprise one or more foaming agents in order to improve visual effect of developer solution on detection. Examples of envisioned foaming agent include, but are not limited to decylamine oxide (e.g. Ammonyx™ DO), lauramine oxide (e.g. Ammonyx™ LO), myristyl dimethylamine oxide (e.g. Ammonyx™ MO), cocoamidopropylamine oxide (e.g. Ammonyx™ CDO special). In embodiments, the developer solution comprises about 0.05% w/w to about 10% w/w foaming agent, or about 0.1% w/w to 5% w/w about foaming agent, or about 0.5% w/w to about 1.5% w/w foaming agent.

The developer solution may also comprise one or more stabilizers in order to improve the stability of the developer solution. Examples of envisioned stabilizer include, but are not limited to 1-hydroxyethylidiene-1,1-diphosphonic acid (HEDP) (e.g. Dequest™ 2010). In embodiments, the developer solution comprises about 0.001% w/w to about 5% w/w stabilizer, or about 0.01% w/w to about 3% w/w stabilizer, or about 0.05% w/w to about 1% w/w stabilizer.

The developer solution may also comprise one or more dyes in order to improve the contrast (e.g. visual detection) between the foam and the product. Examples of envisioned dye include, but are not limited to disodium 6-hydroxy-5-[(2-methoxy-5-methyl-4-sulfophenyl)azo]-2-naphthalenesulfonate (FD&C red 40), ethyl-[4-[[4-[ethyl-[(3-sulfophenyl) methyl]amino]phenyl]-(2-sulfophenyl) methylidene]-1-cyclohexa-2,5-dienylidene]-[(3-sulfophenyl) methyl] azanium (FD&C blue 1), ethyl-[4-[[4-[ethyl-[(3-sulfophenyl) methyl]amino]phenyl]-(4-hydroxy-2-sulfophenyl) methylidene]-1-cyclohexa-2,5-dienylidene]-[(3-sulfophenyl) methyl]azanium (FD&C Green 3). In embodiments, the developer solution comprises about 5 ppm to about 100 ppm dye, or about 10 ppm to about 75 ppm dye, or about 20 ppm to about 50 ppm dye.

According to one particular embodiment, the developer solution according to the invention is composed according to the following table:

TABLE 2A

Developer solution

| Components | CAS number | Role | Concentration (% w/w) |
|---|---|---|---|
| Xanthan gum | 11138-66-2 | Ticking agent | 0-2 |
| Sodium hydroxide | 1310-73-2 | base | 0-1 |
| Hydrogen Peroxide | 7722-84-1 | oxidizer | 0.5-50 |
| HEDP | 2809-21-4 | Stabilizer | 0-5 |
| Amine oxide | 61788-90-7 | Foaming agent | 0.05-10 |
| Demineralized water | — | solvent | to complete to 100% |

According to a preferred embodiment, the developer solution according to the invention is composed according to the following table:

TABLE 2B

Developer solution

| Components | CAS number | Role | Concentration (% w/w) |
|---|---|---|---|
| Xanthan gum | 11138-66-2 | Ticking agent | 0.4 |
| Sodium hydroxide | 1310-73-2 | base | 0.4 |
| Hydrogen Peroxide | 7722-84-1 | oxidizer | 3 |
| HEDP | 2809-21-4 | Stabilizer | 0.8 |
| Amine oxide | 61788-90-7 | Foaming agent | 0.9 |
| Demineralized water | — | solvent | 94.5 |
| pH | | | Adjusted to about 7.5 |

The developer solution may be formulated as an aqueous solution or as a powder for later dissolution in a suitable aqueous solution (e.g. water). The developer solution may be formulated as a ready to use solution or as a liquid concentrate (e.g. 2×, 3×, 4×, 5×, 10× etc.) for further dilution. For a composition formulated as a liquid and/or solid ingredient may be mixed with a predetermined volume of filtered or distilled water. If necessary, the resulting mixed solution may be adjusted to the desired pH by addition of suitable acidifying agents.

Vaporization

Preferably, the enzymatic solution and/or the developer solution are applied on the surface by vaporization or spray. More preferably, the solution(s) is(are) contained in a handheld vaporizer or handheld spray bottle capable of delivering preferably a mist of fine liquid particles on the surface. Other means such as a wipe or pad may be envisioned but are less advisable, as they could cause cross-contamination and/or will generate waste. In addition these wastes may be considered like biohazard materials since they could potentially be contaminated once having been in contact with the surface.

Preferably the vaporizer or spray bottle will distribute a sufficient amount to allow a quick and visually easy detection. In one embodiment, a handheld vaporizer or handheld spray bottle is used to distribute about 0.25 ml to about 0.30 ml of solution in one spray. Preferably the nozzle and quantity distributed is such that the spray will cover a diameter of at least about 0.5 cm to about 60 cm, preferably about 5 cm or 30 cm, when sprayed at a distance of about 2 to 40 cm of the surface.

Regarding the enzymatic solution, the amount to be applied on the surface should not be too high in order to avoid a slow evaporation of the solution. Indeed, the greater the amount of solution, the longer the time of evaporation to dryness. Also, if the amount of solution is too high the solution will tend to drip when applied to vertical surfaces. In embodiments, the enzymatic solution and developer solution may comprise one or more thickening agents in order to improve adhesion of the enzymatic solution on vertical surfaces. In embodiments, the enzymatic solution is let dry for at least 15 sec. or at least 30 sec., or at least 1 min., or at least 90 sec., or at least 2 min. or at least 5 min. or at least 10 min., or at least 15 min., or at least 20 min., or at least 30 min, or at least 60 mi or more. It may also be envisioned to let dry the enzymatic solution for many hours or days, before cleaning the surface and/or applying the developer solution on the surface.

Kit

A further aspect of the invention relates to kits, e.g. cleanness detection kits. The kits of the invention may be useful for the practice of the methods of the invention, particularly for determining cleanness of a surface in hospitals, restaurants, food processing facilities, slaughterhouses, laboratories, etc. as described herein.

A kit of the invention may comprise one or more of the following components: (i) an enzymatic solution comprising catalase, and (ii) a developer solution comprising hydrogen peroxide, as described hereinbefore.

The kit may also comprise additional components, including but not limited to: a user manual or instructions, a spray bottle, pen(s), marking sheets, boxes, holders, cleaning solutions, wipes, etc.

Those skilled in the art will recognize, or be able to ascertain, using no more than routine experimentation, numerous equivalents to the specific procedures, embodiments, claims, and examples described herein. Such equivalents are considered to be within the scope of this invention, and covered by the claims appended hereto. The invention is further illustrated by the following examples, which should not be construed as further or specifically limiting.

EXAMPLES

The examples set forth herein below provide exemplary methods and results showing development, feasibility and utility of the methods, compositions and/or kits, according to the invention.

Example 1

Accelerating Evaporation of the Enzymatic Solution

A study was carried out to assess evaporation of the enzymatic solution in presence or absence of a solvent and/or a surfactant. The following formulations were prepared and tested:

TABLE 3

| | Enzymatic solution | | |
|---|---|---|---|
| | Formulation number | | |
| | 2294.27 | 3294.27 | 1296.27 |
| Demineralized water | 33.305 g | 48.305 g | 33.355 g |
| Isopropanol | 15 g | — | 15 g |
| Propylene glycol | 1 g | 1 g | 1 g |
| Kathon ™ CG/ICP II (1.25%) | 0.015 g | 0.015 g | 0.015 g |
| Bio-Soft ™ E678 (85%) | 0.05 g | 0.05 g | 0 g |
| Terminox ™ Ultra 200L | 0.63 g | 0.63 g | 0.63 g |

The results of the tests are illustrated in FIG. 3. As can be seen, the speed of evaporation increased in presence of a surfactant (Bio-Soft™ E678; formulation no. 2294.27 vs. no. 1296.27). Also, presence of a solvent (isopropanol) increased the evaporation (formulation no. 2294.27 vs. no. 3294.27).

Example 2

Long Term Stability of the Enzymatic Solution

A study was carried out to assess long term stability of the enzymatic solution, in presence of various concentrations of a stabilizer. The following formulations were prepared and tested at room temperature:

TABLE 4

| | Enzymatic solutions | | | | | |
|---|---|---|---|---|---|---|
| | Formulation number | | | | | |
| | 1299.27 | 2299.27 | 3299.27 | 4299.27 | 5299.27 | 6299.27 |
| Demineralized water | 68.62 g | 68.12 g | 67.62 g | 67.12 g | 66.62 g | 66.12 g |
| Isopropanol | 30 g | 30 g | 30 g | 30 g | 30 g | 30 g |
| Propylene glycol | 0 g | 0.5 g | 1 g | 1.5 g | 2 g | 2.5 g |
| Kathon ™ CG/ICP II (1.25%) | 0.03 g | 0.03 g | 0.03 g | 0.03 g | 0.03 g | 0.03 g |
| Bio-Soft ™ E678 (85%) | 0.1 g | 0.1 g | 0.1 g | 0.1 g | 0.1 g | 0.1 g |
| Terminox ™ Ultra 200L | 1.25 g | 1.25 g | 1.25 g | 1.25 g | 1.25 g | 1.25 g |

The results of the tests are illustrated in FIG. 4. As can be seen, enzymatic activity is relatively stable at all the tested concentrations of propylene glycol. It was calculated that the combined average loss of activity over 60 days was about 100 U, or only about 2.6%, a value within the experimental error of the measurements.

Using a diluted solution comprising 2.5 times less catalase (i.e. equivalent to a "loss" of 60% of the original activity), visual detection with the developer solution was still possible due to the formation of bubbles and a foam. However, the speed of the reaction was slower.

Altogether, these results confirm that the enzymatic solution is stable in the long term and useful for real-life and commercial applications (i.e. long term stability required through the steps of manufacture, shipping, storage, distanced repeated uses, etc.).

Headings are included herein for reference and to aid in locating certain sections. These headings are not intended to limit the scope of the concepts described therein, and these concepts may have applicability in other sections throughout the entire specification. Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise. Thus, for example, reference to "a compound" includes one or more of such compounds, and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contains certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A kit for determining the cleanness of a surface comprising:

an enzymatic solution as defined below

| Components | Concentration (% w/w) |
|---|---|
| Catalase | 0.001-19 |
| stabilizer | 0.01-10 |
| Surfactant | 0.01-5 |
| Solvent | 5-65 |
| Demineralized water | To complete to 100% | wherein the stabilizer is propylene glycol, the solvent is isopropanol and the surfactant is Ethoxylated C12-15 alcohols; and a developer solution comprising hydrogen peroxide and a foaming agent.

2. The kit of claim 1, wherein the enzymatic solution and/or the developer solution is(are) contained in a handheld vaporizer or handheld spray bottle.

3. The kit of claim 1, wherein the enzymatic solution comprises about 40 units of catalase per gram of the solution to about 900000 units of catalase per gram of the solution.

4. The kit of claim 1, wherein the enzymatic solution comprises about 25% w/w to about 50% w/w solvent.

5. The kit of claim 1, wherein the enzymatic solution comprises about 0.05% w/v to about 0.5% w/w surfactant.

6. The kit of claim 1, wherein the enzymatic solution has a pH between 4 and 11.

7. The kit of claim 1, wherein the catalase in the enzymatic solution is in the form of a solution comprising at least one of a buffer, a preservative, and a thickening agent.

8. The kit of claim 1, wherein the developer solution comprises about 0.05% w/w to about 50% w/w hydrogen peroxide.

9. The kit of claim 1, wherein the foaming agent of the developer solution is selected from the group consisting of decylamine oxide, lauramine oxide, myristyl dimethylamine oxide, and cocoamidopropylamine oxide.

10. The kit of claim 1, wherein the developer solution comprises about 0.05% w/w to about 10% w/w foaming agent.

11. The kit of claim 1, wherein the developer solution has a pH between 4 and 9.

12. The kit of claim 1, wherein the developer solution further comprises at least one of a dye, a buffer, a preservative, a stabilizer and a thickening agent.

13. Previously presented. An enzymatic solution as defined below:

| Components | Concentration (% w/w) |
|---|---|
| Catalase | 0.001-19 |
| stabilizer | 0.01-10 |
| Surfactant | 0.01-5 |
| Solvent | 5-65 |
| Demineralized water | To complete to 100% | wherein the stabilizer is propylene glycol, the solvent is isopropanol and the surfactant is Ethoxylated C12-15 alcohols.

14. A kit for determining the cleanness of a surface comprising:

an enzymatic solution comprising catalase as defined below

| Components | Concentration (% w/w) |
|---|---|
| Catalase | 0.001-19 |
| stabilizer | 0.01-10 |
| Surfactant | 0.01-5 |
| Solvent | 5-65 |
| Demineralized water | To complete to 100% | wherein the stabilizer is propylene glycol, the solvent is isopropanol and the surfactant is Ethoxylated C12-15 alcohols; and a developer solution comprising hydrogen peroxide and about 0.05% w/w to about 10% w/w foaming agent selected from the group consisting of decylamine oxide, lauramine oxide, myristyl dimethylamine oxide, and cocoamidopropylamine oxide wherein the enzymatic solution and/or the developer solution is(are) contained in a handheld vaporizer or handheld spray bottle.

* * * * *